(12) United States Patent
Headley

(10) Patent No.: US 6,296,602 B1
(45) Date of Patent: Oct. 2, 2001

(54) METHOD FOR COLLECTING PLATELETS AND OTHER BLOOD COMPONENTS FROM WHOLE BLOOD

(75) Inventor: Thomas D. Headley, Wellesley, MA (US)

(73) Assignee: Transfusion Technologies Corporation, Natick, MA (US)

( * ) Notice: Subject to any disclaimer, the term of this patent is extended or adjusted under 35 U.S.C. 154(b) by 0 days.

(21) Appl. No.: 09/271,601

(22) Filed: Mar. 17, 1999

(51) Int. Cl.$^7$ ........................................ B01D 17/00
(52) U.S. Cl. ........................ 494/37; 494/10; 494/45; 604/6.01
(58) Field of Search ........................ 494/7, 9, 37, 45, 494/1, 10; 604/6.01, 6.04

(56) References Cited

U.S. PATENT DOCUMENTS

| | | |
|---|---|---|
| 2,661,150 | 12/1953 | Abbott, Jr. . |
| 3,096,283 | 7/1963 | Hein . |
| 3,239,136 | 3/1966 | Hein . |
| 3,244,362 | 4/1966 | Hein . |
| 3,244,363 | 4/1966 | Hein . |
| 3,456,875 | 7/1969 | Hein . |
| 3,737,096 | 6/1973 | Jones et al. . |
| 4,007,871 | 2/1977 | Jones et al. . |
| 4,010,894 | 3/1977 | Kellogg et al. . |
| 4,056,224 | 11/1977 | Lolachi . |
| 4,082,217 | 4/1978 | Westberg . |
| 4,086,924 | 5/1978 | Latham, Jr. . |
| 4,142,670 | 3/1979 | Ishimaru et al. . |
| 4,151,844 | 5/1979 | Cullis et al. . |
| 4,285,464 | 8/1981 | Latham, Jr. . |
| 4,300,717 | 11/1981 | Latham, Jr. . |
| 4,303,193 | 12/1981 | Latham, Jr. . |
| 4,321,921 | 3/1982 | Laszczower . |
| 4,387,848 | 6/1983 | Kellogg et al. . |
| 4,430,072 | 2/1984 | Kellogg et al. . |
| 4,447,221 | 5/1984 | Mulzet . |
| 4,457,747 | 7/1984 | Tu . |
| 4,482,342 | 11/1984 | Lueptow et al. . |
| 4,530,691 | 7/1985 | Brown . |
| 4,643,714 | 2/1987 | Brose . |
| 4,647,279 | 3/1987 | Mulzet et al. . |
| 4,680,025 | 7/1987 | Kruger et al. . |
| 4,708,712 | 11/1987 | Mulzet . |
| 4,734,089 | 3/1988 | Cullis . |
| 4,806,252 | 2/1989 | Brown et al. . |
| 4,850,995 | 7/1989 | Tie et al. . |
| 4,889,524 | 12/1989 | Fell et al. . |
| 4,911,833 | 3/1990 | Schoendorfer et al. . |
| 4,934,995 | 6/1990 | Cullis . |
| 4,940,543 | 7/1990 | Brown et al. . |
| 4,968,295 | 11/1990 | Neumann . |
| 4,983,158 | 1/1991 | Headley . |
| 4,985,153 | 1/1991 | Kuroda et al. . |
| 5,039,401 | 8/1991 | Columbus et al. . |
| 5,045,048 | 9/1991 | Kaleskas et al. . |
| 5,112,298 | 5/1992 | Prince et al. . |
| 5,114,396 | 5/1992 | Unger et al. . |
| 5,141,486 | 8/1992 | Antwiler . |
| 5,154,716 | 10/1992 | Bauman et al. . |
| 5,174,894 | 12/1992 | Ohsawa et al. . |
| 5,217,426 | 6/1993 | Bacehowski et al. . |

(List continued on next page.)

*Primary Examiner*—John Kim
*Assistant Examiner*—Richard W. Ward
(74) *Attorney, Agent, or Firm*—Bromberg & Sunstein LLP

(57) ABSTRACT

A method for collecting, from whole blood, platelets suspended in plasma. By centrifuging the blood at a high enough rotational speed, the platelets are separated from the plasma and the red blood cells. In a preferred embodiment, some of the plasma is removed while the centrifuge is being spun to keep the platelets separated from the plasma. Then, the speed of rotation is altered so as to cause the platelets to mix with the remaining plasma. The platelets can then be collected with the remaining plasma.

15 Claims, 3 Drawing Sheets

U.S. PATENT DOCUMENTS

| | | |
|---|---|---|
| 5,217,427 | 6/1993 | Cullis . |
| 5,234,403 | 8/1993 | Yoda et al. . |
| 5,273,517 | 12/1993 | Barone et al. . |
| 5,277,701 | 1/1994 | Christie et al. . |
| 5,298,016 | 3/1994 | Gordon . |
| 5,300,060 | 4/1994 | Nelson . |
| 5,316,540 | 5/1994 | McMannis et al. . |
| 5,318,512 | 6/1994 | Neumann . |
| 5,368,542 | 11/1994 | McMannis et al. . |
| 5,386,734 | 2/1995 | Pusinelli . |
| 5,387,174 | 2/1995 | Rochat . |
| 5,387,187 | 2/1995 | Fell et al. . |
| 5,417,650 | 5/1995 | Gordon . |
| 5,437,598 | 8/1995 | Antwiler . |
| 5,470,483 | 11/1995 | Bene et al. . |
| 5,484,396 | 1/1996 | Naficy . |
| 5,505,685 * | 4/1996 | Antwiler . |
| 5,543,062 | 8/1996 | Nishimura . |
| 5,651,766 | 7/1997 | Kingsley et al. . |
| 5,728,060 | 3/1998 | Kingsley et al. . |
| 5,733,253 | 3/1998 | Headley et al. . |
| 5,733,545 * | 3/1998 | Hood, III . |
| 5,779,660 | 7/1998 | Kingsley et al. . |
| 5,964,724 * | 10/1999 | Rivera et al. . |

\* cited by examiner

METHOD FOR COLLECTING PLATELETS AND OTHER BLOOD COMPONENTS FROM WHOLE BLOOD

TECHNICAL FIELD

This invention generally relates to systems and methods for processing blood and other biological fluids.

BACKGROUND ART

FIG. 1 shows a typical disposable bag set used in the prior art to collect platelets from whole blood. The set includes a needle 10 or cannula, which is inserted into a vein of a donor. The needle 10 is connected to the tube 11, which in turn is connected to collection bag 12, so as to allow whole blood to flow from the donor through the needle 10 and the tube 11 into collection bag 12. The collection bag 12 contains anticoagulant. After the desired amount of blood has been collected into collection bag 12, the needle 10 is removed from the donor, and tube 11 is cut and heat sealed. The remainder of the bag set is then brought to a centrifuge, which spins the bag set so that the blood in collection bag 12 separates into platelet-rich plasma and red blood cells. Typically, the centrifuge is not located at the point where the blood donation takes place.

After the blood has separated into platelet-rich plasma and red blood cells (RBCs), the bag set is removed from the centrifuge. The platelet-rich plasma is urged from collection bag 12 through tube 13 into platelet-storage bag 14. The tube 13 leading to the platelet- and plasma-storage bags 14, 15 is then cut and heat sealed. Storage-solution bag 16 holds RBC-storage solution. After the platelet-rich plasma has been urged into the platelet-storage bag 14, the RBC-storage solution is urged from the storage-solution bag 16 into the collection bag 12. The tube 41 connecting the collection and storage-solution bags 12, 16 is then cut and heat sealed.

At this stage, the bag set has been divided into two portions: (i) the first portion consists of the collection bag 12, which now holds primarily red blood cells (along with storage solution), filter 17, RBC-storage bag 18, and the tubing 19 that connects these components, and (ii) the second portion consists of the platelet-storage bag 14, which now holds platelet-rich plasma, and the plasma-storage bag 15 and the tubing that connects these two components.

The first portion may be hung, so that gravity causes the RBC component to pass from the collection bag 12 through the filter 17 to RBC-storage bag 18. The filter 17 removes white blood cells (WBCs) from the red blood cells. After the red blood cells (and storage solution) pass into the RBC-storage bag 18, tube 19 is cut and heat sealed.

To collect platelets, the second portion is centrifuged at a high rotational speed in order to separate the platelets from the plasma. After the platelets have been separated from the plasma, some of the plasma is urged from the platelet-storage bag 14 into the plasma-storage bag 15. Typically, 50 mls of plasma are left with the platelets in the platelet-storage bag 14. After the desired amount of plasma has been removed from the platelet-storage bag 14 to the plasma-storage bag 15, the tube connecting these two bags is cut and heat sealed. Thus, at the end of the procedure, the platelet-storage bag 14 holds platelets in about 50 ml of plasma, the plasma-storage bag 15 holds platelet-poor plasma, and the RBC-storage bag 18, of course, holds red blood cells.

This prior-art process of collecting and separating blood components involves many steps and frequent human intervention. The arrangement of the prior-art bag set does not permit the process to be easily automated.

SUMMARY OF THE INVENTION

The present invention is directed to systems and methods for collecting, from whole blood, platelets suspended in plasma. By centrifuging the blood at a high enough rotational speed, the platelets are separated from the plasma and the red blood cells. In a preferred embodiment, some of the plasma is removed while the centrifuge is being spun to keep the platelets separated from the plasma. Then, the speed of rotation is altered so as to cause the platelets to mix with the remaining plasma. The platelets can then be collected with the remaining plasma.

A system that may be used for carrying out the invention includes a centrifuge rotor, a flow-control arrangement and a spinner. The flow-control arrangement introduces whole blood into the centrifuge rotor and removes blood components from the centrifuge rotor. A controller causes the spinner to rotate at two different speeds: The rotor is spun at a first speed so as to separate the blood into a first component, a second component and a third component. The first component is primarily plasma. The second component is located, while the rotor is being spun, outside of the first component and is primarily red blood cells. The third component is located, while the rotor is being spun, between the first and second components and includes platelets. The controller causes the rotor's speed of rotation to be altered so as to cause the third component to mix with the first component. The controller also causes the flow-control arrangement to remove from the rotor a portion of the plasma containing platelets.

As noted above, in a preferred embodiment, the controller causes the flow-control arrangement to remove some of the first component (the plasma) before the third component (comprising the platelets) is mixed with the first component. The system also preferably includes a plasma-volume determination sensor in communication with the controller; the plasma-volume determination sensor determines the volume of the first component in the rotor. The controller may thus remove a portion of the first component based on the determined volume of the first component.

DESCRIPTION OF SPECIFIC EMBODIMENTS

Figure 1:
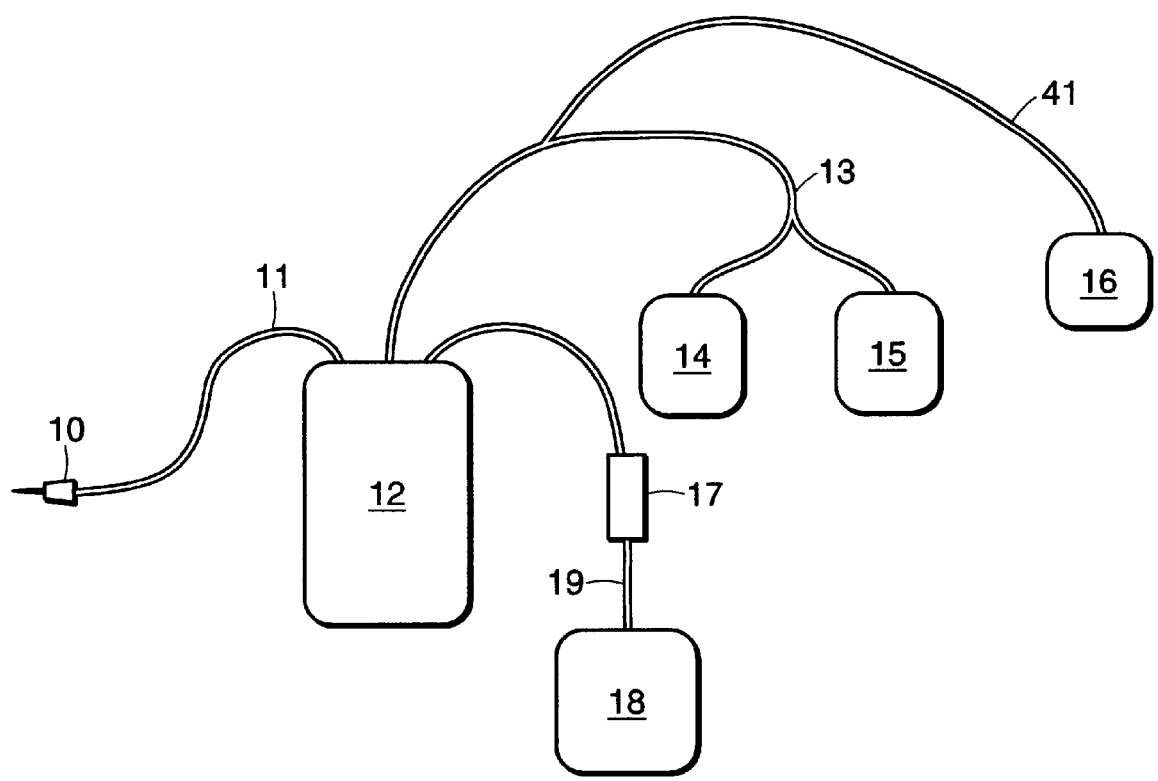
FIG. 1 shows a disposable set that may be used in a prior-art system for collecting platelets from whole blood.
Figure 2:
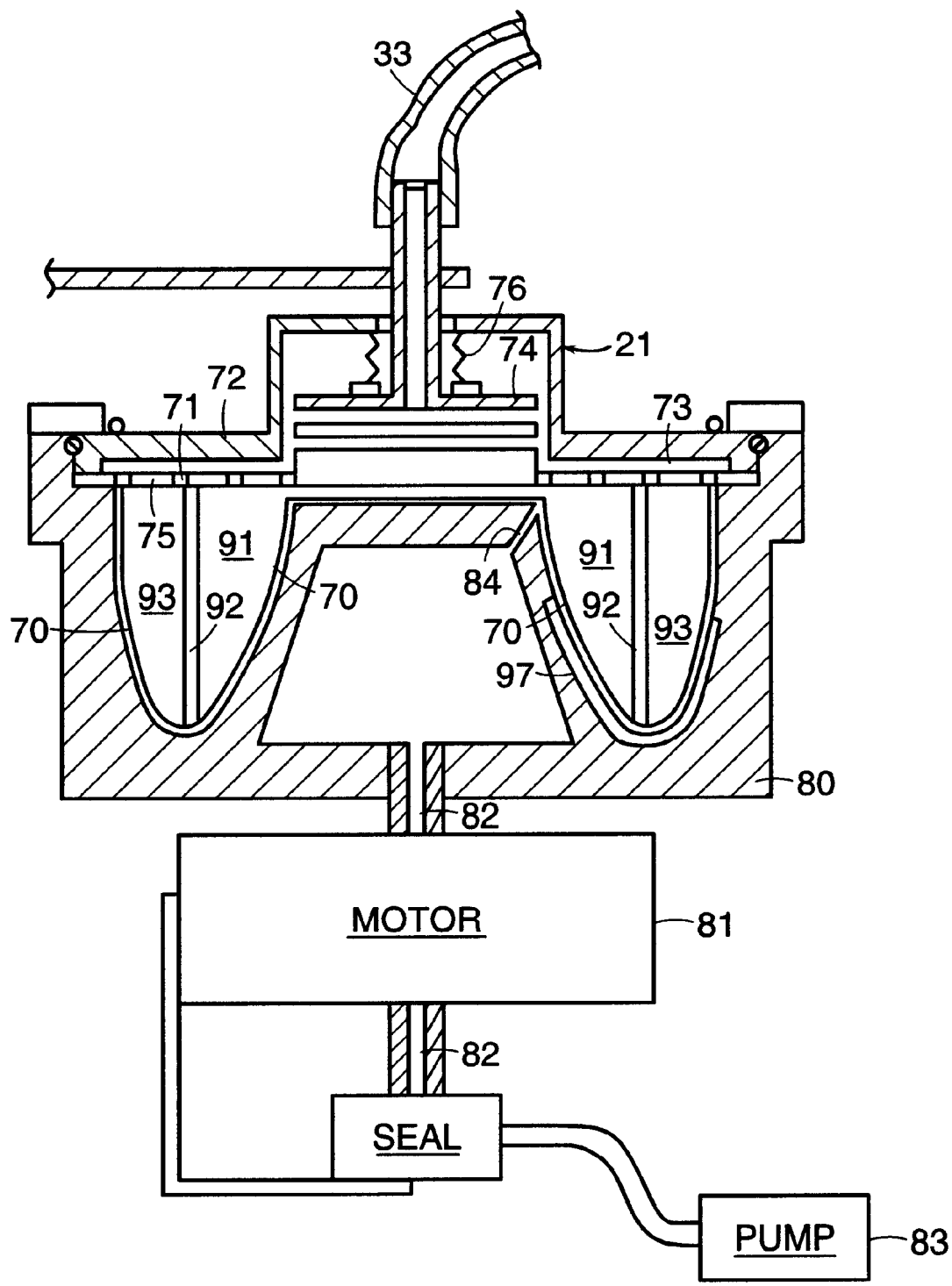
FIG. 2 shows a cross-sectional view of a variable-volume rotor mounted in a chuck that spins the rotor and causes the rotor's volume to change.

A method of collecting platelets is described in connection with FIG. 2. FIG. 2 shows a cross-section of a rotor 21 mounted in a chuck 80, which is located in the control unit and which holds the rotor 21. This rotor 21 may be any one of a variety of designs, but preferably the rotor has a variable total volume, such as the rotors shown and described in U.S. Pat. No. 5,733,253 (which is incorporated herein by reference). (The rotor shown in FIG. 2 is similar to the rotor shown in FIGS. 1–4 of U.S. Pat. No. 5,733,253, but it will be appreciated that other designs, such as other designs shown in U.S. Pat. No. 5,733,253, may be used instead.) A motor 81 causes the chuck 80 and the rotor 21 to spin. The control unit also includes a pump 83, which is connected through the cannulated axis 82 of the motor 81 to the interior of the chuck 80. The rotor 21 has an elastic diaphragm 70, which defines the interior volume of the rotor 21. Upper boundary wall 72 also defines the interior volume of the rotor 21. The position of the diaphragm 70 determines the volume of the rotor, and the position of the diaphragm 70 may be controlled by controlling, by means of the pump 83, the pressure of the gas in the interior of the chuck 80. The interior of the chuck 80 includes one or more apertures 84 to permit the gas to come into fluid communication with the diaphragm 70. The rotor 21 may also include a interior wall 75 with perforations 71. The boundary wall 72 and the interior wall 75 form a passage 73, through which blood and blood components may flow to and from the rotor's non-rotating portion 74 and the tubing 33 attached to the rest of the disposable set. A rotary seal 76 provides a seal between the rotating and non-rotating portions of the rotor 21. In lieu of the perforated interior wall 75, channels may be located on the interior surface of the boundary wall 72 to provide fluid communication between the rotor's non-rotating portion 74 and the outer radius of the rotor's interior (as shown in FIGS. 41 and 42 of above-referenced U.S. Pat. No. 5,733,253).

FIG. 2 shows the rotor 21 at its maximum volume, with the diaphragm 70 stretched as far as the chuck 80 permits it to be stretched. The rotor 21 is spun sufficiently fast by the chuck 80 and the motor 81 to cause the blood to be separated into red blood cells 93, platelets 92 and plasma 91. Since, of these three blood components, the RBC component 93 of the blood has the greatest specific gravity, the RBC component is the furthest from the rotor's axis of rotation. The plasma component 91 has the lightest specific gravity, and therefore the plasma component is the closest to the axis of rotation. The platelet component 92, having an intermediate specific gravity, forms a thin layer between the plasma and RBC components.

In order to collect the platelets, it is preferable first to collect all but about 50 milliliters of the plasma. The remaining 50 mls of plasma will be used to store the platelets, as the standard practice in the industry is to store a unit of platelets in 50 mls of plasma. The plasma 91 is collected (i.e., urged through fixed portion 74 to tube 33) by continuing to spin the rotor 21 and using the pump 83 to increase the pressure against the diaphragm 70, and/or by slowing the revolutions of the rotor 21. The rotor 21 should preferably continue to be spun quickly and smoothly enough to keep the platelets 92 in a separate layer.

Once all but 50 mls of plasma 91 has been collected, the platelets 92 may be mixed with the remaining plasma by sharply changing the speed of rotation of the rotor 21. It has been found that, by sharply changing the rotor's speed of rotation, the platelets will mix with the neighboring plasma. Because the red blood cells have a much heavier specific gravity, the red blood cells tend to remain in their separate layer. Of course, the rotor's speed must not be altered so radically and quickly as to cause the red blood cells as well to mix with the other components. Alternatively, the speed of rotation may be slowed sufficiently—although not necessarily sharply—so that the platelets mix with the plasma but the red blood cells remain separate. Once the platelets are mixed with the remaining plasma, additional pressure may be created by the pump 83 to push the diaphragm 70 further outward and force the platelets, now suspended in plasma, out of the rotor into tube 33. The red blood cells may then be collected. Each of the components, platelets suspended in plasma, platelet-poor plasma, and the red blood cells should be directed to a separate container. Alternatively, one or both of the platelet-poor plasma and the red blood cells may be returned to the donor.

Figure 3:
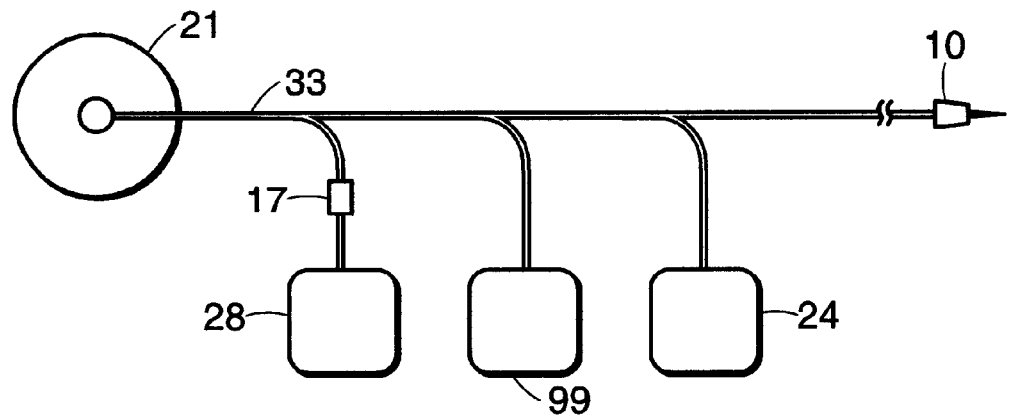
FIG. 3 shows a disposable set using a variable-volume rotor, such as the one in FIG. 2.

FIG. 3 shows a disposable set that may be used in the platelet-collection process just described. The disposable set includes the rotor 21, a plasma-storage container 24, a platelet-storage container 99, a RBC-storage container 28, a filter 17 for removing white blood cells from the red blood cells, a cannula 10 (or other means for permitting whole blood to enter the disposable set), and tubing 33 connecting these components. The plasma-storage container 24 may contain anticoagulant, which may be introduced into the whole blood as it is being drawn through the needle 10 to the rotor 21. The platelet-storage container 99 may contain platelet-storage solution, and the RBC-storage container 28 may contain RBC preservative. After the plasma and the platelets have been removed from the rotor 21, the RBC preservative may be urged from the RBC-storage container 28 into the rotor 21, where the RBC preservative is mixed with the red blood cells remaining in the rotor 21. The red blood cells and the preservative may then be urged from the rotor 21 through the filter 17 into the RBC-storage container 28, in the manner described in concurrently filed application, Ser. No. 09/271,594, for a "System and Method for Separating Blood Components," and listing Headley and Powers as inventors. (This application is incorporated herein by reference.) Alternatively, the present invention may be used with the system and process described in concurrently filed application, Ser. No. 09/271,627, for a "System and Method for Red-Blood-Cell Apheresis," and listing James Cianci as the inventor. (This application is also incorporated herein by reference.)

Figure 4:
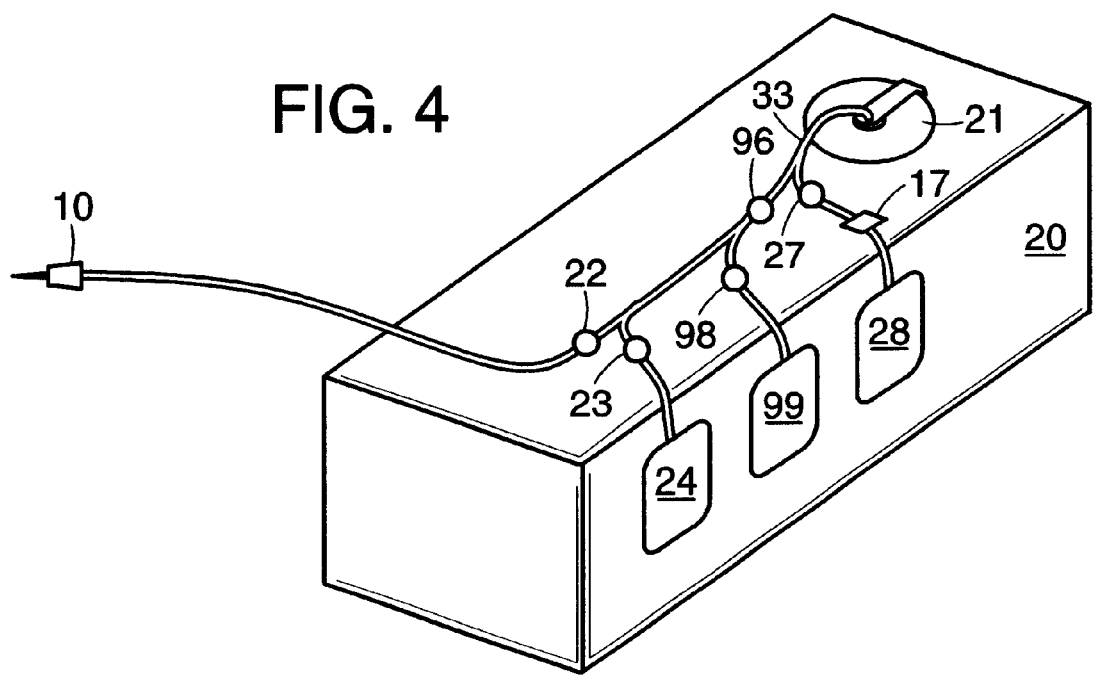
FIG. 4 shows a control unit holding the disposable of FIG. 3.

FIG. 4 shows the disposable set of FIG. 3 mounted in a control unit 20. The control unit 20 includes a flow-control arrangement for controlling and/or causing flow between the needle 10, the rotor 21 and the storage containers 24, 99, 28. The flow-control arrangement may include valves 22, 23, 98, 27, which control the flow through the various branches of the tubing. Alternatively, a single valving cassette may be used to control the flow through the various branches of the tubing. For instance, applying a vacuum on the rotor's diaphragm while valve 22 is open helps draw blood from the donor into the rotor 21. In addition to or in lieu of changing the pressure against the rotor's diaphragm, the control unit may be provided with independent pumping mechanisms (such as a peristaltic pump) that act on the tubing (or on a valving cassette) to force fluid through the tubing in the desired direction.

In order to determine how much plasma should be removed in order to leave only 50 mls of plasma, in which the platelets are to be suspended, the control unit may be provided with an arrangement for determining the volume of the red blood cells. One means of determining the volume of the red blood cells is to provide an array 97 of optical sensors (shown in FIG. 2) in the chuck 80 to determine the radius of the inner boundary of the red blood cells 93 when the blood has been centrifuged into different components. (If the boundary wall 72 is translucent, the array may be mounted above the rotor 21 instead of below it.) The control unit 20 may then calculate the volume of the red blood cells based on the location of this boundary when the rotor is filled with, say, one unit of blood. Using this volume information, the control unit may determine approximately the weight of the red blood cells in the rotor, based on the specific gravity of red blood cells.

By weighing the chuck/rotor combination before and after the whole blood was introduced into the rotor, the control unit may determine the weight of all the blood components in the rotor when the rotor is filled. By subtracting the weight of the red blood cells from the total weight of all the blood components in the rotor, the control unit may determine approximately the weight of the plasma in the rotor, and how much of it should be removed in order to leave approximately 50 mls of plasma in the rotor. By weighing the chuck/rotor combination as platelet-poor plasma is being urged from the rotor, or alternatively by weighing the container 24 that holds the plasma as it leaves the rotor, the control unit can stop removing plasma when the correct amount of plasma has been removed. The platelet-poor plasma is preferably directed to the plasma-storage container 24.

At that point, there should be approximately 50 mls of plasma left in the rotor, as well as all the platelets and all the red blood cells. The speed of the rotor may then be changed rapidly, in order to cause the platelets 92 to become mixed in the approximately 50 mls of the plasma remaining. The platelet/plasma combination is then urged from the rotor and sent to the platelet-storage container 99. Another optical sensor 96, mounted on the outlet tube 33 senses when the red blood cells start emerging from the rotor. (See FIG. 4.) When the red blood cells are detected, flow to the platelet-collection container 99 is stopped, and the red blood cells may be directed through filter 17 to a RBC-collection container 28.

Although the invention has been described with reference to several preferred embodiments, it will be understood by one of ordinary skill in the art that various modifications can be made without departing from the spirit and the scope of the invention, as set forth in the claims hereinbelow.

What is claimed is:

1. A method of collecting platelets comprising:
   providing a centrifuge rotor having a variable total volume;
   introducing whole blood into the centrifuge rotor;
   determining a weight of the whole blood introduced into the rotor;
   spinning the rotor at a first speed so as to separate the blood into a first component, a second component and a third component, wherein the first component is primarily plasma, wherein the second component is located, while the rotor is being spun, outside of the first component and is primarily red blood cells, and wherein the third component is located, while the rotor is being spun, between the first and second components and includes platelets;
   removing from the rotor a weight of first component;
   determining as a function of the weight of the whole blood, the weight of first component to remove;
   changing the rotor's speed of rotation so as to cause the third component to mix with first component remaining in the rotor; and
   removing from the rotor a portion of the plasma containing platelets.

2. The method of claim 1 wherein determining a weight of the whole blood comprises weighing the centrifuge rotor before and after introducing the whole blood.

3. The method of claim 1 wherein removing a weight of first component further comprises weighing the removed first component.

4. The method of claim 1 wherein removing a weight of first component further comprises weighing the centrifuge rotor as the first component is removed to measure the amount of first component that has been removed.

5. The method of claim 1 further comprising approximately determining weight of red blood cells in the rotor during said spring at the first speed.

6. The method of claim 5 wherein approximately determining comprises sensing volume of red blood cells in the rotor and calculating weight of red blood cells from the volume based on specific gravity of the red blood cells.

7. The method of claim 5 wherein determining the weight of first component comprises calculating the amount of first component to remove so as to leave a desired amount of plasma in the rotor, the calculation being a function of the given weight of the whole blood and the determined weight of the red blood cells.

8. A method of collecting platelets from whole blood, the method comprising:
   providing a disposible set having an inlet, a platelet container, a centrifuge rotor having a variable total volume, and tubing connecting the inlet, the platelet container and the rotor;
   providing a control unit having a spinner in which the rotor may be held;
   placing the rotor in the spinner;
   drawing whole blood through the inlet;
   directing the whole blood from the inlet through the tubing to the rotor;
   determining a weight of the whole blood directed into the rotor;
   causing the spinner to rotate the rotor so as to separate the whole blood into a first component, a second component and a third component, wherein the first component is primarily plasma, wherein the second component is located, while the rotor is being spun, outside of the first component and is primarily red blood cells, and wherein the third component is located, while the rotor is being spun, between the first and second components and includes platelets;
   removing from the rotor a weight of first component determining as a function of the weight of the whole blood the weight of first component to remove;
   altering the rotor's speed of rotation so as to cause the third component to mix with the first component; and
   urging a mixture of the first and third components out of the rotor, while the rotor is still spinning.

9. The method according to claim 8, wherein whole blood is drawn through the inlet and directed to the rotor while the rotor is mounted in the spinner.

10. The method according to claim 9, wherein the centrifuge rotor is provided with a fixed portion, a rotatable portion and a rotary seal providing a seal between the fixed and rotatable portions, and the tubing is connected to the rotor's fixed portion.

11. The method according to claim 10, wherein the control unit varies the volume of the centrifuge rotor.

12. The method according to claim 11, wherein the centrifuge rotor is provided with a flexible diaphragm which defines the volume of the rotor, and the control unit is provided with means for varying air pressure adjacent the flexible diaphragm so as to vary the total volume of the centrifuge rotor.

13. The method according to claim 8, wherein the centrifuge rotor is provided with a fixed portion, a rotatable portion and a rotary seal providing a seal between the fixed and rotatable portions, and the tubing is connected to the rotor's fixed portion.

14. The method according to claim 8, wherein the disposable set includes a plasma-storage container and an RBC container, the method further comprising:

directing a portion of the first component to the plasma-storage container and the third component to the RBC container.

15. The method according the claim 8, wherein the disposable set includes return means, the method further comprising:

directing at least one of the first and second components back to a whole blood donor through the return means.

\* \* \* \* \*